(12) United States Patent
Schweiger et al.

(10) Patent No.: US 10,179,120 B2
(45) Date of Patent: Jan. 15, 2019

(54) DOSAGE REGIMEN OF FERRIC TRIMALTOL

(71) Applicant: Iron Therapeutics Holdings AG, Wollerau (CH)

(72) Inventors: Christian Schweiger, Wollerau (CH); Carl Andrew Sterritt, Wollerau (CH); Julian David Howell, Wollerau (CH)

(73) Assignee: Iron Therapeutics Holdings AG, Wollerau (CH)

( * ) Notice: Subject to any disclaimer, the term of this patent is extended or adjusted under 35 U.S.C. 154(b) by 0 days.

(21) Appl. No.: 15/110,003

(22) PCT Filed: Jan. 6, 2015

(86) PCT No.: PCT/IB2015/050098
§ 371 (c)(1),
(2) Date: Jul. 6, 2016

(87) PCT Pub. No.: WO2015/101971
PCT Pub. Date: Jul. 9, 2015

(65) Prior Publication Data
US 2016/0324822 A1 Nov. 10, 2016

(30) Foreign Application Priority Data

Jan. 6, 2014 (GB) .................................. 1400171.3
Oct. 21, 2014 (GB) .................................. 1418708.2

(51) Int. Cl.
| | |
|---|---|
| *A61K 31/351* | (2006.01) |
| *A61K 33/26* | (2006.01) |
| *A61K 9/48* | (2006.01) |
| *A61K 47/02* | (2006.01) |
| *A61K 47/12* | (2006.01) |
| *A61K 47/20* | (2006.01) |
| *A61K 47/26* | (2006.01) |
| *A61K 47/32* | (2006.01) |

(52) U.S. Cl.
CPC .............. *A61K 31/351* (2013.01); *A61K 9/48* (2013.01); *A61K 33/26* (2013.01); *A61K 47/02* (2013.01); *A61K 47/12* (2013.01); *A61K 47/20* (2013.01); *A61K 47/26* (2013.01); *A61K 47/32* (2013.01)

(58) Field of Classification Search
CPC ...... A61K 31/351; A61K 47/32; A61K 47/26; A61K 47/20; A61K 9/48; A61K 47/02; A61K 47/12; A61K 33/26
See application file for complete search history.

(56) References Cited

U.S. PATENT DOCUMENTS

| | | | |
|---|---|---|---|
| 6,339,080 B1 | 1/2002 | Stockham et al. | |
| 2008/0234226 A1 | 9/2008 | Erichsen et al. | |
| 2014/0088064 A1* | 3/2014 | Stockham ............ | A61K 31/351 514/184 |
| 2017/0304314 A1 | 10/2017 | Mallard et al. | |

FOREIGN PATENT DOCUMENTS

| | | |
|---|---|---|
| JP | S58-159421 A | 9/1983 |
| JP | 2000-229860 A | 8/2000 |
| JP | 2001-505928 A | 5/2001 |
| JP | 2006-063086 A | 3/2006 |
| JP | 2007-505146 A | 3/2007 |
| JP | 2008-539729 A | 11/2008 |
| JP | 2009-515909 A | 4/2009 |
| JP | 2013-032308 A | 2/2013 |
| WO | 2002024196 A1 | 3/2002 |
| WO | 2009138761 A1 | 11/2009 |
| WO | WO-2012101442 | 8/2012 |
| WO | 2015/101971 A1 | 7/2015 |

OTHER PUBLICATIONS

Reffitt et al., "Assessment of iron absorption from ferric trimaltol" Ann. Clin. Biochem, 2000, 37(4):457-466.
Harvey et al., "Ferric trimaltol corrects iron deficiency anaemia in patients intolerant of iron" Alimentary Pharmacology & Therapeutics, 1998, 12(9): 845-848.
Anonymous: "Oral ferric iron for iron deficiency anaemia in ulcerative colitis", EFCCA, 2011.
Gasche et al. "DOP079. Correcting iron deficiency anaemia in IBD: A Pivotal phase 3 study of a novel oral ferric iron" Europ. Crohn's and Colitis Organisation, ECCO, 2014, DOP Session 9-Therapy Today.
Anonymous: "Ferric trimaltol: Phase III data", BioCentury Week in Review, clinical results, 2014.
International Search Report and Written Opinion issued in PCT/IB2015/050098 dated Jun. 10, 2015.
Bergamaschi et al., "Prevalence and pathogenesis of anaemia in inflammatory bowel disease . . . " Haematologica 95:199-205, 2010.
Brise et al., "Absorbability of different iron compounds" Acta Med. Scand. 171(Suppl 376):23-37, 1962.
Kerr et al., "Gastrointestinal Intolerance to Oral Iron Preparations" Lancet ii:489-92, 1958.
Slivka et al., "Rapid Communication: Hydroxyl Radicals and the Toxicity of Oral Iron" Biochem. Biopharm. vol. 35 (4):553-6, 1986.
Wilson et al., "Prevalence and outcomes of anaemia in inflammatory bowel disease: A systematic Review of the Literature" Am. J. Med. 116(7a):44S-49S, 2004.
British National Formulary, Nutrition and Blood. BMJ Publishing Group and RPS Publishing, London 51:463-504, 2006.

(Continued)

*Primary Examiner* — Sudhakar Katakam
(74) *Attorney, Agent, or Firm* — McCarter & English, LLP; Steven G. Davis; Mei Bai

(57) ABSTRACT

The present invention relates to a dosage regimen of ST10 (ferric trimaltol) for the treatment of patients suffering from iron deficiency with or without anaemia. Specifically the invention relates to the treatment of patients with 30 mg ST10 twice daily.

11 Claims, 6 Drawing Sheets

(56) References Cited

OTHER PUBLICATIONS

Dudkowiak et al., Hepcidin and its role in inflammatory bowel disease. Adv Clin Exp Med. Jul.-Aug. 2013;22(4):585-91.
Kawai et al., A case of ulcerative colitis induced by oral ferrous sulphate. ACTA Paediatr. Jpn. Aug. 1992;34(4):476-8.
Kelsey et al., Absorption of low and therapeutic doses of ferric maltol, a novel ferric iron compound, in iron deficient subjects using a single dose iron absorption test. J Clin Pharm Ther. Apr. 1991;16(2):117-22.
Makrides et al., Efficacy and tolerability of low-dose iron supplements during pregnancy: a randomized controlled trial. Am J Clin Nutr. Jul. 2003;78(1):145-53.
Rimon et al., Are we giving too much iron? Low-dose iron therapy is effective in octogenarians. Am J Med. Oct. 2005;118(10):1142-7.
International Search Report and Written Opinion for Applciation No. PCT/IB2015/058115, dated Jan. 12, 2016.
United Kingdom Search Report for Application No. 1418710.8, dated Jun. 30, 2015.
United Kingdom Search Report for Application No. GB1400171.3, dated Jul. 4, 2014. 4 pages.
Babitt et al., Mechanisms of anemia in CKD. J Am Soc Nephrol. Oct. 2012;23(10):1631-4.

\* cited by examiner

Mean serum concentration-time curves of total Iron after administration of ST10 at 30 mg bid, 60 mg bid and 90 mg bid on day 1

Mean serum concentration-time curves of total iron after administration of ST10 at 30 mg bid, 60 mg bid and 90 mg bid on Day 8

Mean serum value-time curves of transferrin saturation after administration of ST10 at 30 mg bid, 60 mg bid and 90 mg bid on Day 1

Mean serum value-time curves of transferrin saturation after administration of ST10 at 30 mg bid, 60 mg bid and 90 mg bid on Day 8

Mean serum concentration-time curves of soluble transferrin receptor after administration of ST10 at 30 mg bid, 60 mg bid and 90 mg bid on Day 1

Mean serum concentration-time curves of ferritin – change from baseline.

DOSAGE REGIMEN OF FERRIC TRIMALTOL

CROSS-REFERENCE TO RELATED APPLICATIONS

This application is a 35 U.S.C. § 371 national stage filing of International Application No. PCT/IB2015/050098, filed on Jan. 6, 2015, which claims the benefit of United Kingdom Patent Application No. 1400171.3, filed on Jan. 6, 2014, and United Kingdom Patent Application No. 1418708.2, filed on Oct. 21, 2014. The contents of each of the foregoing applications are incorporated herein by reference in their entirety.

The present invention relates to a dosage regimen of ST10 (ferric trimaltol) for the treatment of patients suffering from iron deficiency with or without anaemia. The invention further relates to the treatment of patients with iron deficiency anaemia (IDA) in inflammatory bowel disease (IBD).

BACKGROUND TO THE INVENTION

Iron deficiency anaemia is characterised by low levels of iron in the blood and can be due to insufficient dietary intake of iron, or loss of iron from internal bleeding caused by diseases of the gastrointestinal or urinary tract, for example inflammatory bowel diseases such as Crohn's disease and ulcerative colitis. Ulcerative colitis is a chronic inflammatory disease affecting the colon and anaemia is recognised as a serious complication and symptom of ulcerative colitis. Iron deficiency anaemia (IDA) in inflammatory bowel disease (IBD) is primarily caused by chronic blood loss from inflamed mucosa and/or iron malabsorption in both active and inactive stages of the disease (1). Dietary restriction and highly selective diets amongst IBD patients often result in poor dietary intake, whilst mucosal inflammation in the gastrointestinal tract may lead to inadequate nutrient absorption (2). Characteristic symptoms of IDA in IBD include chronic fatigue, headache and impairment of cognitive function.

Iron deficiency, without anaemia, has also been shown to have clinical consequences for patients and individuals. Iron is an important component of many intracellular processes and the effect of iron deficiency or iron deficiency correction has been reported in chronic heart failure, growth, behaviour and learning in children and cognition in the elderly. When iron deficiency remains untreated it can lead to iron deficiency anaemia.

Typically, treatment for iron deficiency anaemia is in the form of ferrous iron ($Fe^{2+}$) salts, (e.g. ferrous sulphate) dosed orally as 300 mg tablets (60 mg elemental iron) three to four times daily. However, as the duodenum can maximally absorb only 10-20 mg of iron a day, greater than 90% of ingested iron is not absorbed, leading to symptomatic adverse events including toxicity at the gastrointestinal mucosa, abdominal pain, nausea, vomiting, constipation, diarrhoea and dark stools, all of which are dose related and lead to poor adherence with treatment.

In addition if ferrous iron tablets become lodged in the upper gastrointestinal tract contact irritation may occur causing erosion or ulceration. Hence treatment with ferrous iron is badly tolerated leading to poor compliance, particularly in patients suffering from IBD who already have significant damage to their gastrointestinal tract (3-4). In fact, treatment with ferrous iron preparations in such patients can often worsen their condition and lead to treatment of such patients with intravenous iron administration.

Alternative treatment with oral ferric iron ($Fe^{3+}$) salts also results in poor iron absorption due to the ready formation of insoluble chelates when passing from the acidic environment of the stomach to the small intestine. Consequently there is a need to overcome the above-identified problems associated with current oral treatments for iron deficiency anaemia. There is a particular need to develop new orally-dosed iron-based treatments for patients who are intolerant of ferrous iron compositions.

ST10, also referred to as ferric trimaltol and ferric maltol is a chemically stable complex formed between ferric iron ($Fe^{3+}$) and maltol (3-hydroxy-2-methyl-4-pyrone) was developed as an alternative to oral ferrous products and has been shown to correct iron deficiency in subjects with a history of ferrous sulphate intolerance (5). ST10 makes iron available in the gastrointestinal tract, providing iron in a biologically labile form for uptake across the mucus layer and intestinal wall (5). Since the iron is stabilized in a chelated form it is less toxic; therefore together with its high bioavailability, lower doses of elemental iron are administered thereby improving toxicity and patient compliance.

Harvey et al (6) reported single doses of 30 mg ST10 twice daily in patients recruited from gastroenterology clinics, those presenting with active inflammatory disease were excluded from the study.

The inventors have found that a combination of a particular dosage regimen and tablet formulation have led to surprising improvement in haemoglobin levels in patients suffering from iron deficiency with or without anaemia and in addition, from anaemia resulting from Crohn's disease or ulcerative colitis, which were previously intolerant to oral ferrous products. These results have been reported as clinically meaningful even after a short treatment period of four weeks and confirm that ST10 is an effective therapy for iron deficiency anaemia in IBD patients and may be administered safely over a twelve week period or longer with reduced side effects and improved compliance. In addition the inventors have observed fewer common side effects associated with ferrous iron treatment such as gut related side effects, reduction in blackened stools and compatibility with antacid treatments.

SUMMARY OF THE INVENTION

According to a first aspect of the invention there is provided ST10 for use in the treatment or prevention of iron deficiency with or without anaemia wherein ST10 is administered orally as a 30 mg preparation on an empty stomach twice daily wherein said 30 mg preparation comprises at least 60% of ST10.

According to a further aspect of the invention there is provided a method of treating a patient suffering from iron deficiency with or without anaemia, the method comprising administering orally to the patient a 30 mg ST10 preparation on an empty stomach wherein said 30 mg preparation comprises at least 60% of ST10.

According to a further aspect of the invention there is provided a ST10 formulation comprising 231.5 mg of ST10 and one or more other excipients wherein said ST10 formulation comprises at least 60% of ST10.

DETAILED DESCRIPTION OF THE INVENTION

Figure 1:
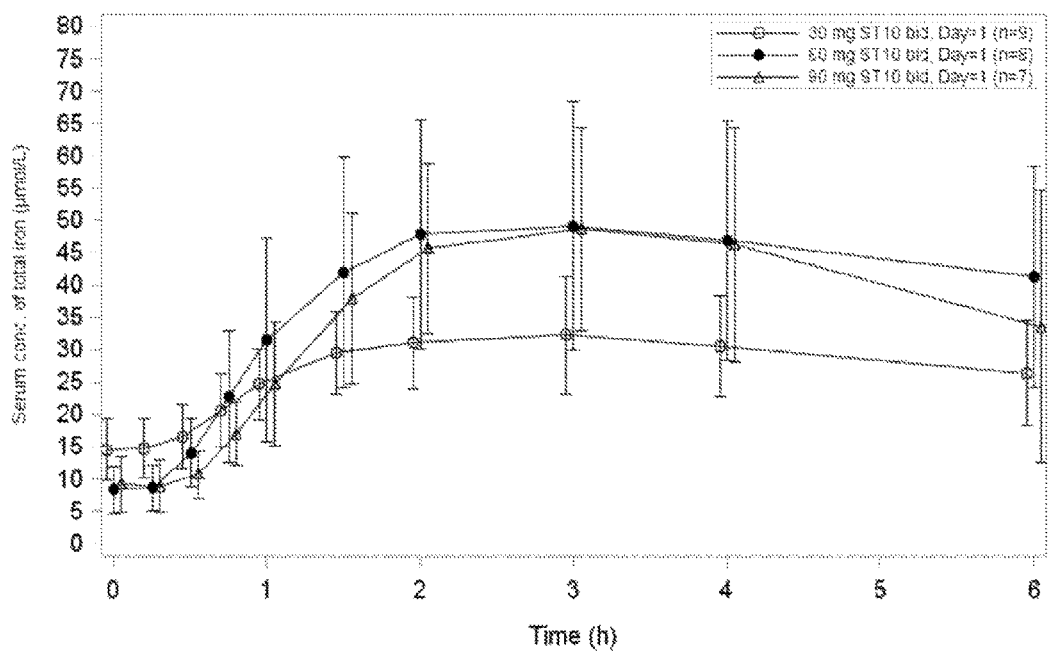
FIG. 1 shows a graph of mean serum concentration of total iron over 6 hours after administration of ST10 at doses of 30 mg bid, 60 mg bid, 90 mg bid on day 1.

According to a first aspect of the invention there is provided ST10 for use in the treatment or prevention of iron deficiency with or without anaemia wherein ST10 is administered orally as a 30 mg preparation on an empty stomach twice daily wherein said 30 mg preparation comprises at least 60% of ST10.

In one embodiment of the invention there is provided ST10 for use in the treatment or prevention of iron deficiency anaemia in inflammatory bowel disease wherein ST10 is administered orally as a 30 mg preparation on an empty stomach twice daily wherein said 30 mg preparation comprises at least 60% of ST10.

ST10 is also known as ferric trimaltol and ferric maltol is a chemically stable complex formed between ferric iron ($Fe^{3+}$) and maltol (3-hydroxy-2-methyl-4-pyrone) according to the chemical structure below.

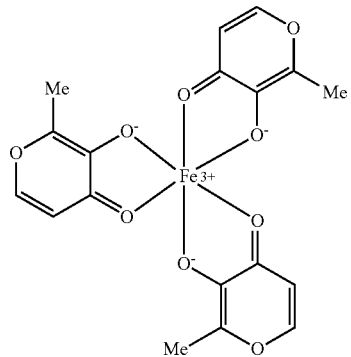

The molar ratio of iron to hydroxypyrone is 1:3

Maltol is a naturally occurring sugar derivative and is used in the food industry as a flavour enhancer. ST10 may be administered as a 30 mg dose, where 30 mg refers to the amount of elemental iron in the dose. The amount of ST10 equivalent to 30 mg of elemental iron ($Fe^{3+}$) is 231.5 mg.

The dose may comprise varying amounts of other excipients for example lactose monohydrate, sodium lauryl sulphate, crospovidone, colloidal silicon dioxide, colloidal silicon dioxide and magnesium stearate.

The ST10 preparation may be comprised within a capsule or tablet and mixed with a pharmaceutically acceptable carrier for example suitable diluents, excipients or carriers selected with regard to oral administration. ST10 may be combined with an oral, non-toxic, inert carrier such as lactose, gelatin, agar, starch, sucrose, glucose, dicalcium phosphate, calcium sulfate, mannitol, sorbitol and microcrystalline cellulose. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol and waxes. Lubricants used in these dosage forms may include sodium oleate, sodium stearate, sodium benzoate, sodium acetate, sodium chloride, stearic acid, sodium stearyl fumarate, and talc. Disintegrators include, without limitation, starch, methyl cellulose, agar, bentonite, xanthan gum, croscarmellose sodium, and sodium starch glycolate.

In one embodiment the 30 mg ST10 preparation comprises:
231.5 mg ST10
91.5 mg lactose monohydrate
3.0 mg sodium lauryl sulphate
9.0 mg crospovidone
0.6 mg colloidal silicon dioxide
3.0 mg magnesium stearate In another aspect the 30 mg ST10 preparation comprises:
231.5 mg ST10
80-110 mg lactose monohydrate
3.0 mg sodium lauryl sulphate
9.0 mg crospovidone
0.6 mg colloidal silicon dioxide
3.0 mg magnesium stearate The percentage of ST10 is at least 60% of the combined weight of ST10 and excipients.

The ST10 preparation may be comprised within a capsule. In one example the capsule is a hard gelatin capsule.

The inventors have found that by significantly reducing the amount of lactose monohydrate in the preparation it was possible to reduce the overall size of the capsule without compromising on efficacy and absorption of the ST10 active ingredient. The new capsule formulation is smaller and easier to administer thereby improving patient compliance and tolerability.

The capsule size may vary to effectively contain ST10 and the excipients. For example the capsule size may be defined as a size 1 capsule and has a volume of approximately 0.5 ml, a length of approximately 19.4 mm and a diameter of approximately 6.91 mm. Slight variations to these dimensions are included within the scope of the invention.

30 mg ST10 preparation may be administered as an oral preparation for example as a tablet or capsule formulation. In one example the 30 mg ST10 preparation is administered as a size 1 capsule.

For the avoidance of doubt reference herein to administering a ST10 dose to a patient, refers to administering to a mammal, preferably a human.

30 mg ST10 preparation may be administered orally daily or twice daily on two separate occasions during the waking hours provided that the capsule is taken on an empty stomach. This is to reduce the likelihood of ST10 forming precipitates with food elements. In one example the ST10 dose is administered once before breakfast and once prior to sleep. Administration at these times of the day is known to improve patient compliance and reduces the risk of side effects attributed to excess iron. Dosing on an empty stomach allows for lower dosage of elemental iron and consequently improved tolerability and therefore provides a significant improvement in reduction of side effects and patient compliance. Ferrous iron in comparison has to be taken with food to mask the associated gastrointestinal symptoms and is therefore given in much larger daily doses.

In one embodiment the ST10 dose is administered orally. The ST10 dose may be administered as a solid dosage form or as a liquid formulation. An example of a suitable liquid formulation is provided in GB1404390.5.

30 mg ST10 preparation may be administered once daily, or once every two, three, four, five, six or seven days.

30 mg ST10 preparation may administered in the range of 10 mg to 120 mg once daily or once every two, three, four, five, six or seven days.

The inventors have found that certain advantageous effects associated with ST10 treatment have been observed which have not previously been reported. In particular it was noted that patients in the study of Example 1 did not report blackened stools, which is a recognised side effect of ferrous iron treatment and is caused by excess iron in the gut and faeces. This observation provides a significant advantage in terms of disease monitoring and prognosis, particularly for patients who are suffering from IBD and have upper gastrointestinal bleeding, or subjects with IDA secondary to bleeding from upper GI sources (e.g. oesophageal varices; gastric ulcer) since it allows clinicians to differentiate between bleeding related to gastrointestinal disease and excess iron in the gastrointestinal tract from the ferrous iron treatment. Therefore ST10 treatment is amenable to ongoing long term or maintenance treatment since it allows clinicians to associate blackened stools with disease pathogenesis.

Furthermore it is appreciated that ST10 provides iron through the normal physiological route as it is swallowed and absorbed across the gut wall. Iron absorbed through ST10 is therefore under normal physiological control and is down-regulated through fewer iron transporting proteins available at the enterocyte luminal surface in subjects who have normal levels of iron. In this way overload and toxicity of iron is not a potential risk for ST10 unlike conventional ferrous treatments. The low risk of iron overload provides another advantage for long term maintenance treatment using ST10 and provides another safety advantage in the event of an overdose. Iron treatments are commonly prescribed to women of child-bearing age and there exists a risk to paediatric safety in the event of an overdose. The risk is significantly reduced for ST10 because the levels of elemental iron are much lower in comparison to ferrous products which if overdosed in children can result in death due to liver failure.

30 mg ST10 preparation may be administered for a period of four weeks, a period of three weeks or a period of two weeks until iron levels have increased to normal levels. 30 mg ST10 preparation may be administered for any period until iron levels have increased to normal levels. For example a 30 mg ST10 dose may be administered from a period of up to 16 weeks, but can be administered for as long as needed.

30 mg ST10 preparation may be administered indefinitely as a maintenance dose.

In one embodiment ST10 is for use in the treatment or prevention of iron deficiency anaemia in inflammatory bowel disease wherein said ST10 is administered orally as a 30 mg size 1 capsule on an empty stomach twice daily, once before breakfast and once prior to sleep for up to a twelve week period wherein the percentage of ST10 is at least 60% of the combined weight of ST10 and excipients.

In another embodiment ST10 is for use in the treatment or prevention of iron deficiency with or without anaemia wherein said ST10 is administered orally as a 30 mg size 1 capsule on an empty stomach twice daily, once before breakfast and once prior to sleep for up to a twelve week period wherein the percentage of ST10 is at least 60% of the combined weight of ST10 and excipients.

ST10 is also amenable to combination therapies. For example it is known to combine iron supplements with hormonal contraception tablets to treat anaemia in child bearing women who suffer from menorrhagia. Such combinations carry a risk of non-compliance when combined with ferrous iron since the gastrointestinal side effects could lead to non-compliance and risk of pregnancy. ST10 may be safely combined with hormone contraceptive tablets since the observed side effects seen for ferrous iron are not observed.

ST10 for use in the treatment or prevention of iron deficiency anaemia in women suffering from menorrhagia.

In this aspect ST10 may be administered in accordance with the any of the previous aspects described herein.

ST10 may be administered at the same time as antacid treatment, for example compounds containing calcium, magnesium, and proton pump inhibitors (PPIs). ST10 doses may also be administered in diseases or situations that result in reduced or lack of gastric acid production for example after gastrectomy, in old age or atrophic or autoimmune gastritis. In contrast ferrous tablets should not be taken with stomach pH raising medications as this reduces the bioavailability of iron from ferrous products.

The ST10 doses described herein are useful in the treatment of iron deficiency with or without anaemia. For the avoidance of doubt, iron deficiency with or without anaemia relates to all diseases and conditions associated with iron deficiency and for which treatment with iron would be therapeutically beneficial. Such diseases are those which are recognised as having iron deficiency as a complication or symptom. Iron deficiency is also referred to as sideropenia or hypoferremia and results from a prolonged period of inadequate iron intake; this medical state is called Latent Iron deficiency (LID) or Iron-deficient Erythropoiesis (IDE).

Symptoms of iron deficiency can be apparent before iron deficiency anaemia and include but are not limited to fatigue, hair loss, twitches, irritability, dizziness, brittle or grooved nails, appetite disorders such as pica and pagophagia, impaired immune function, chronic heart failure, growth, behaviour and learning in children, cognition in the elderly and Plummer-Vinson syndrome (PVS).

The studies described herein report the treatment of subjects having active inflammatory disease or acute chronic inflammation. In previous studies reported, some patients were excluded because the production of cytokines in states of chronic inflammation, such as IL-10, lipopolysaccharide, TNF-alpha and hepcidin act via multiple mechanisms to increase the uptake and storage of iron in the reticuloendothelial system, and reduce the uptake of iron from the gut. It is appreciated that inflammatory bowel diseases (IBD) such as Crohn's disease and ulcerative colitis may be in the active or flare state as described above, or in remission. Patients recruited into the most recent clinical study (as described in Example 1) demonstrated a range of inflammatory states of IBD as measured by recognised and validated IBD disease activity scales. Patients with ulcerative colitis had to have a Simple Clinical Colitis Activity Index (SCCAI) of up to 4; and patients with Crohn's disease had a Crohn's Disease Activity Index (CDAI) of up to 220, and thus classified as having mild or moderate disease at inclusion into the study. The disease activity in the overall population of patients is notable in that approximately one third of subjects were being treated with anti-TNF biological therapy.

A subject may be characterised as having active inflammatory disease or acute chronic inflammation by having a Simple Clinical Colitis Activity Index (SCCAI) of up to 4 or a Crohn's Disease Activity Index (CDAI) of up to 220.

Conditions associated with iron deficiency anaemia include, but are not limited to chronic kidney disease (CKD), Systemic Lupus (SLE), rheumatoid arthritis, haematological cancers (e.g. Hodgkin's disease), chronic bacterial infection (e.g. osteomyelitis), viral hepatitis, HIV, AIDS, diseases of the gastrointestinal tract for example inflammatory bowel diseases (IBD) such as Crohn's disease and ulcerative colitis.

In one embodiment the 30 mg ST10 dose described herein is useful in the treatment of iron deficiency with or without anaemia, wherein the iron deficiency is a result of, or associated with active inflammatory disease or acute chronic inflammation.

In a further embodiment there is provided ST10 for use in the treatment or prevention of active inflammatory disease or acute chronic inflammation wherein ST10 is administered orally as a 30 mg preparation twice daily.

In a further example, there is provided ST10 for use in the treatment or prevention of iron deficiency with or without anaemia, wherein the iron deficiency is a result of, or associated with active inflammatory disease or acute chronic inflammation wherein ST10 is administered orally as a 30 mg dose twice daily wherein the percentage of ST10 is at least 60% of the combined weight of ST10 and excipients.

The presence of active inflammatory disease or acute chronic inflammation can be determined by a physician using known methods, for example the recognised UC and CD clinical disease activity scales (SCCAI and CDAI).

In another embodiment the 30 mg ST10 dose described herein are useful in the treatment of chronic kidney disease (CKD). One of the recognised symptoms of this condition is iron deficiency with and without anaemia and so the ST10 dosages described herein provide a safe, effective and manageable treatment for subjects who are already taking one or more other medications.

In another aspect the invention relates to a method of treating a patient suffering from iron deficiency anaemia associated with inflammatory bowel disease, the method comprising administering orally to the patient a 30 mg ST10 preparation on an empty stomach, wherein the percentage of ST10 is at least 60% of the combined weight of ST10 and excipients.

In one embodiment there is provided a method of treating a patient suffering from iron deficiency with or without anaemia, the method comprising administering orally to the patient a 30 mg ST10 preparation on an empty stomach, wherein the percentage of ST10 is at least 60% of the combined weight of ST10 and excipients.

In addition to IBD, ST10 has use in the treatment of diseases resulting in iron deficiency including but not limited to disease associated with the urinary tract and renal function.

In another aspect the invention relates to a 30 mg ST10 formulation comprising 231.5 mg ST10 and one or more excipients wherein the percentage of ST10 is at least 60% of the combined weight of ST10 and excipients.

The 30 mg ST10 formulation may comprise
231.5 mg ST10
91.5 mg lactose monohydrate
3.0 mg sodium lauryl sulphate
9.0 mg crospovidone
0.6 mg colloidal silicon dioxide
3.0 mg magnesium stearate Example 1

128 patients suffering from IDA were randomised. Of this group 67 were suffering from Crohn's disease and 53 were suffering from ulcerative colitis. All had mild to moderate disease activity and anaemia associated with IBD which was measured according to low haemoglobin levels (9.5-12 d/dL for women and 13 g/dL (male) and were intolerant of ferrous iron, or it could not be used. There were no restrictions on the use of gastric pH modifying agents or medications.

60 patients were treated with ST10 at a 30 mg dose twice daily, before breakfast and prior to sleep on an empty stomach for a period of 12 weeks.

60 patients received a matched placebo capsule and were treated in the same way for the same period. Withdrawal from the study before 12 weeks occurred in seven ST10 subjects and nine placebo subjects. 87% of subjects completed 12 weeks of treatment.

Results

Mean Hb levels increased by 2.26 g/dL in ST10-treated subjects from baseline (mean Hb 11.10 g/dL [SD 1.03]) to Week 12 (mean Hb 13.20 g/dL [SD 1.04]) compared to no change in placebo treated subjects from baselines (mean Hb 11.10 g/dL [SD 0.85]) to week 12 (mean Hb 11.15 g/dL [SD 1.04)]. The results for the ST10 group showed a mean improvement of 2.25 g/dL ($p<0.0001$) representing the change from baseline for ST10 compared to placebo at week 12. More than 65% of subjects treated with ST10 experience normalised haemoglobin levels by week 12. The ST10 group also showed significant improvements of haemoglobin levels at week 4 (1.05 g/dL, $p<0.0001$) and 8 weeks (1.75 g/dL, $p<0.0001$) of therapy.

Adverse events recorded in the study were mainly gastrointestinal in nature and occurred in the ST10 treated group with placebo-like frequency (38% of ST10 treated subjects and 40% placebo treated subjects).

109 of the 128 subjects were treated with 30 mg ST10 twice daily for up to 64 weeks. Adverse reactions were seen in 23% of subjects, the most frequent reactions were gastrointestinal symptoms (abdominal pain, flatulence constipation and diarrhoea).

The baseline disease activity score (SCCAI and CDAI) was not related to the degree of Hb correction, and was also not related to whether patients were being treated with anti-TNF therapies.

The results conclude that treatment with ST10 does not adversely affect IBD symptoms and is well tolerated for the duration of the treatment.

Example 2

These studies were primarily pharmacokinetic and conducted in subjects with iron deficiency having active inflammatory disease or acute chronic inflammation. An open-label, randomised, single and repeat dose parallel group Phase I pharmacokinetic study was carried out to evaluate the effect of single and repeated twice daily (bid) oral doses of ST10 at 30 mg, 60 mg and 90 mg for 8 days.

24 subjects with iron deficiency (with or without anaemia) were randomly allocated to one of the three ST10 dose groups as follows:

Group 1: 9 subjects received ST10, 30 mg twice daily for 7 days (days 1-7) plus a final 30 mg dose on the morning of day 8.

Group 2: 8 subjects received ST10, 60 mg twice daily for 7 days (days 1-7) plus a final 60 mg dose on the morning of day 8.

Group 3: 7 subjects received ST10, 90 mg twice daily for 7 days (days 1-7) plus a final 90 mg dose on the morning of day 8.

On day 1, following fasting for at least 1.5-2 hours beforehand, ST10 was administered (30 mg, 60 mg or 90 mg) and blood samples collected over the following 6 h for analysis. 60 mg was administered as two 30 mg capsules and 90 mg was administered as three 30 mg capsules, both as a single dose. Subjects continued dosing with ST10 on the evening of day 1 then every morning and evening for the next 6 days (Days 2 to 7).

On day 8 following fasting for at least 1.5-2 hours beforehand the last dosing of ST10 was administered (30 mg, 60 mg or 90 mg) and blood samples collected over the following 6 h for analysis.

On Days 1 and 8 blood samples were collected predose (0 h=time of ST10 dose) and at 5 minutes (for NTBI only), 15 minutes, 30 minutes, 45 minutes, and 1, 1.5, 2, 3, 4 and 6 h postdose.

Serum concentrations of transferrin, total iron binding capacity (TIBC), ferritin and soluble transferrin receptor; and reticulocyte haemoglobin concentrations (CHr) in whole blood were measured by central laboratories using appropriately validated methods.

These studies used transferrin saturation and total serum iron as measurements of iron uptake from the gut into the transport mechanisms. In addition serum ferritin was used as a measure of iron storage status at the end of the dosing period; all of these measurements are standard and well recognised.

One subject in the 60 mg dose group prematurely withdrew from the study on Day 7, so full profiles of all serum iron parameters were available in the 30 mg dose group for 9 subjects (days 1 and 8), in the 60 mg dose group 8 subjects on day 1 and for 7 subjects on day 8, and in the 90 mg dose group for 7 subjects (days 1 and 8).

Results

Total Iron Serum Concentration and Total Iron Binding Capacity.

Figure 2:
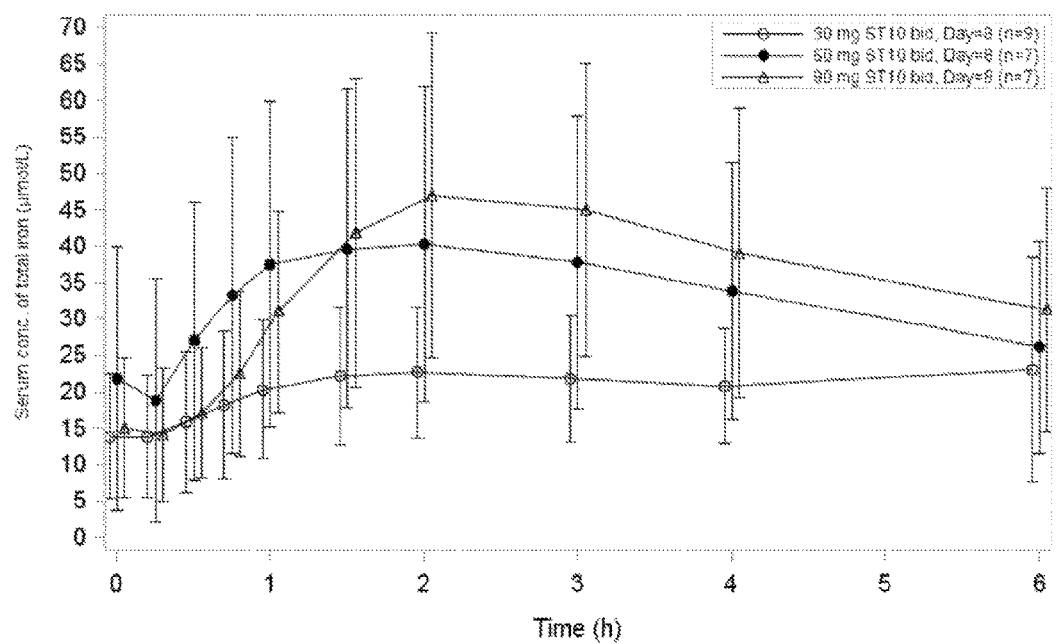
FIG. 2 shows a graph of mean serum concentration of total iron over 6 hours after administration of ST10 at doses of 30 mg bid, 60 mg bid, 90 mg bid on day 8.

Maximum serum concentrations of total iron were reached between 2 and 3 h postdose. Initially a slight decline in serum total iron concentrations was observed, followed by an increase to on average 32.3, 49.1 and 48.7 µmol/L on Day 1 for the 30 mg, 60 mg and 90 mg dose groups, respectively. Serum total iron concentrations gradually declined after reaching $t_{max}$ (time to reach the maximal observed analyte concentration) and mean serum concentrations were 11.8, 33.0 and 24.3 µmol/L above baseline at 6 h postdose on Day 1 for the 30 mg, 60 mg and 90 mg dose groups, respectively. Comparable serum concentrations were measured on Day 8. (FIGS. 1 and 2)

Total iron binding capacity remained fairly constant over time and between dose groups with a mean concentration of approximately 70 µmol/L and individual values ranged between 47 and 101 µmol/L.

The results indicate that doses of 30 mg and above are well tolerated and allow for a high level of iron absorption.

Transferrin and Transferrin Saturation (TSAT)

Transferrin binds iron reversibly in the plasma and transports it into the cell via binding to the transferrin receptor. An increased plasma transferrin level is an indicator of iron deficiency anaemia.

Figure 3:
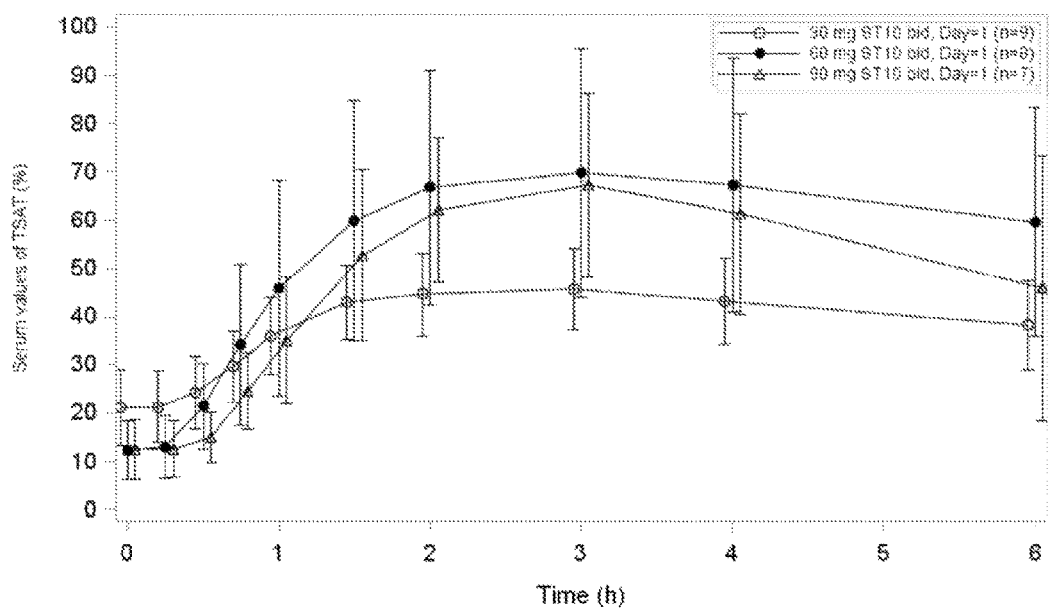
FIG. 3 shows a graph of mean serum values over 6 hours of transferrin saturation after administration of ST10 at doses of 30 mg bid, 60 mg bid, 90 mg bid on day 1.
Figure 4:
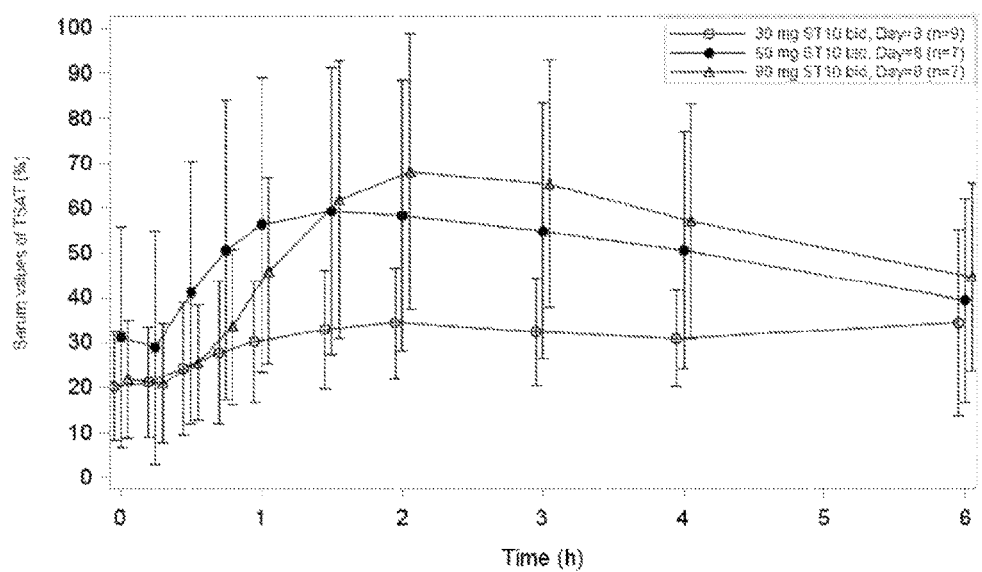
FIG. 4 shows a graph of mean serum values over 6 hours of transferrin saturation after administration of ST10 at doses of 30 mg bid, 60 mg bid, 90 mg bid on day 8.

Maximum serum values of TSAT were reached between 2 and 3 h post-dose. Transferrin saturation values gradually increased up to an average value of 45.6, 69.8 and 67.3% on Day 1 for the 30 mg, 60 mg and 90 mg dose groups, respectively. Transferrin saturation gradually declined after reaching $t_{max}$ (time to reach the maximal observed analyte concentration) and serum values were 17.0, 47.3 and 33.3% above baseline at 6 h postdose on Day 1 for the 30 mg, 60 mg and 90 mg dose groups, respectively (FIG. 3). Similar TSAT serum values were measured on Day 8 (FIG. 4).

Figure 5:
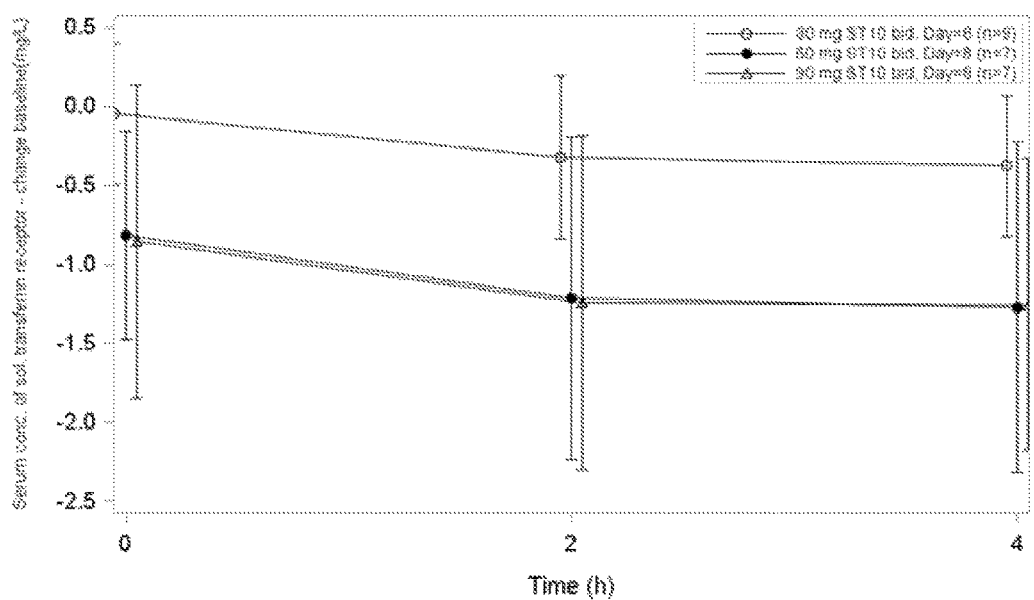
FIG. 5 shows a graph of serum concentration of soluble transferrin receptor over 4 hours after administration of ST10 at doses of 30 mg bid, 60 mg bid, 90 mg bid on days 1-7 and a single dose of 30 mg bid, 60 mg bid, 90 mg on day 8.

Soluble transferrin receptor remained fairly constant over time and between dose groups, with a mean concentration of approximately 4 mg/L and individual values ranged between 1.8 mg/L and 9.3 mg/L. Soluble transferrin receptor concentration decreases in response to iron treatment. FIG. 5 shows no difference between the 60 mg and 90 mg dose, however in comparison the concentration of sTFr is significantly higher for the 30 mg dose, supporting the finding that doses of 30 mg and above are well tolerated and effective.

Ferritin Concentrations

Ferritin is an intracellular protein that stores iron in a soluble and non-toxic form and small amounts are secreted into the serum where it functions as an iron carrier. Hence plasma ferritin is an indirect marker for the total amount of iron stored in the body and can be used to detect iron deficiency. High ferritin levels indicate the presence of excess iron and thus a correction in iron deficiency.

Mean ferritin concentrations remained fairly constant over the individual concentration time profiles, with higher ferritin serum concentrations on day 8 compared to day 1. Mean serum ferritin values for the 30 mg, 60 mg and 90 mg dose groups were around 15 µg/L, 10 µg/L and 13 µg/L on day 1 and 22 µg/L, 22 µg/L and 32 µg/L on day 8, respectively.

Figure 6:
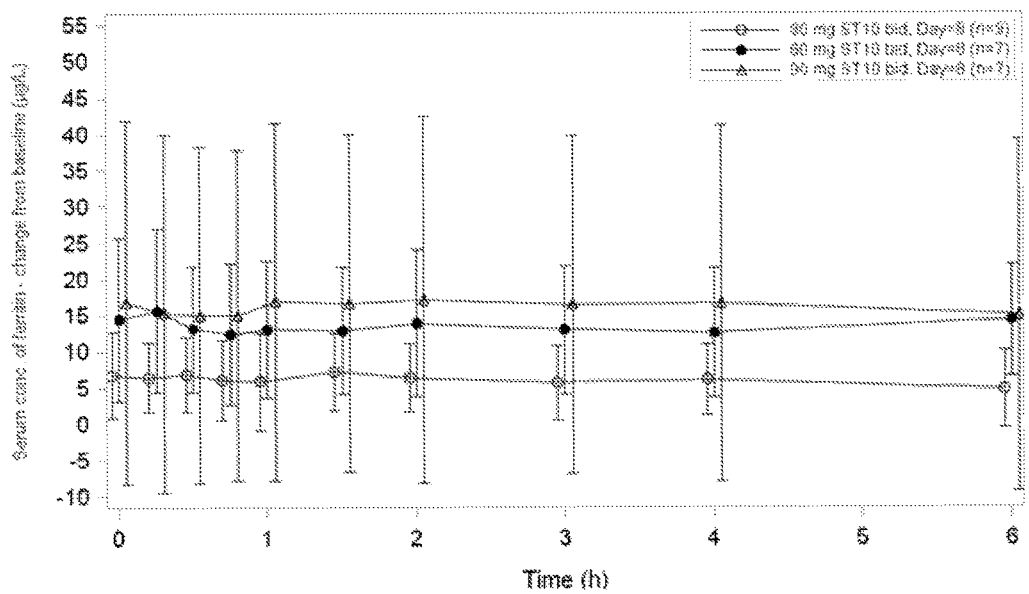
FIG. 6 shows a graph of mean serum concentration of ferritin over 6 hours after administration of ST10 at 30 mg bid, 60 mg bid, 90 mg bid on days 1-7 and a single dose of 30 mg bid, 60 mg bid, 90 mg on day 8.

On day 8 the results show that there were higher concentrations of ferritin in the serum for the 60 mg and 90 mg dose in comparison to the 30 mg dose (FIG. 6).

Reticulocyte Haemoglobin (Hb)

This study measured reticulocyte haemoglobin. Reticulocytes are immature red blood cells, formed in the bone marrow but also found in the circulating blood. They represent less than 5% of the red blood cell mass, but provide an early indicator of change in total haemoglobin Low numbers of reticulocytes or immature red blood cells are a marker for the presence of anaemia and so measurement of the levels of haemoglobin allows progression of treatment for anaemia to be monitored.

TABLE 1

| Dose | Baseline | Day 8 | Mean change |
|---|---|---|---|
| 30 mg bid | 33.6 | 34.6 | 0.9 |
| 60 mg bid | 31.0 | 34.1 | 3.3 |
| 90 mg bid | 30.8 | 33.9 | 3.0 |

In this study we saw that all doses of ST10 gave an increase in reticulocyte haemoglobin (Table 1).

The rate of improvement of Haemoglobin (Hb) content in reticulocytes seen over 8 days is evidence of the incorporation of iron into normal physiological functions and therefore translates to a clinical benefit associated with the dose administered.

REFERENCES

1. Bergamaschi G. et al Prevalence and pathogenesis of anaemia in inflammatory bowel disease. Haematological 2010; 95:199-205
2. Wilson A. et al. Prevalence and outcomes of anaemia in inflammatory bowel disease. A systematic review of the literature. Am J Med 2004; 116(7A):44S-49S.
3. Kerr D N S. et al. Gastrointestinal tolerance to iron. Lancet 1958; ii:489-92.
4. Brise H. et al. Absorbability of different iron compounds. Acta Med scand. 1962; 171 (Suppl. 376): 23-37.
5. Slivka A. et al Hydroxyl radicals and toxicity or oral iron. Biocjem Biopharmacol 1986; 35: 553-6
6. Harvey, R. S. J., et al. Ferric trimaltol corrects iron deficiency anaemia in patients intolerant of iron. Aliment pharmacol Ther 1998: 12: 845-848.

The invention claimed is:

1. A method for the treatment of iron deficiency with or without anaemia in a patient, comprising administering orally to the patient ferric trimaltol as a 30 mg elemental iron preparation on an empty stomach twice daily, wherein the percentage of ferric trimaltol is at least 60% of the combined weight of ferric trimaltol and excipients, wherein iron deficiency with or without anaemia is a result of, or associated with active inflammatory disease or active acute/chronic inflammation.

2. The method of claim 1 wherein iron deficiency is iron deficiency with anaemia in inflammatory bowel disease.

3. The method of claim 2 wherein the inflammatory bowel disease is Crohn's disease.

4. The method of claim 2 wherein the inflammatory bowel disease is ulcerative colitis.

5. The method of claim 1 wherein said ferric trimaltol 30 mg elemental iron preparation is administered once prior to breakfast and once prior to sleep.

6. The method of claim 1 wherein the ferric trimaltol 30 mg elemental iron preparation is administered for up to a twelve week period.

7. The method of claim 6, further comprising administering orally after the twelve week period to the patient ferric trimaltol as a 30 mg-120 mg elemental iron preparation once daily, or once every two, three, four, five, six or seven days.

8. The method of claim 1 wherein the ferric trimaltol 30 mg elemental iron preparation is administered indefinitely as a maintenance dose.

9. The method of claim 1 wherein the ferric trimaltol 30 mg elemental iron preparation is a size 1 capsule.

10. The method of claim 1 wherein the ferric trimaltol 30 mg elemental iron preparation comprises:
   231.5 mg ferric trimaltol,
   91.5 mg lactose monohydrate,
   3.0 mg sodium lauryl sulphate,
   9.0 mg crospovidone,
   0.6 mg colloidal silicon dioxide, and
   3.0 mg magnesium stearate.

11. A method for the treatment of iron deficiency with or without anaemia in a patient, comprising administering orally to the patient ferric trimaltol as a 30 mg elemental iron size 1 capsule on an empty stomach twice daily, once prior to breakfast and once prior to sleep for up to a twelve week period, wherein the percentage of ferric trimaltol is at least 60% of the combined weight of ferric trimaltol and excipients, wherein iron deficiency with or without anaemia is a result of, or associated with active inflammatory disease or active acute/chronic inflammation.

* * * * *